（12) United States Patent
Sethi

(10) Patent No.: US 9,295,423 B2
(45) Date of Patent: Mar. 29, 2016

(54) SYSTEM AND METHOD FOR AUDIO KYMOGRAPHIC DIAGNOSTICS

(71) Applicant: Toshiba America Electronic Components, Inc., San Jose, CA (US)

(72) Inventor: Rakesh Sethi, San Jose, CA (US)

(73) Assignee: Toshiba America Electronic Components, Inc., Irvine, CA (US)

( * ) Notice: Subject to any disclaimer, the term of this patent is extended or adjusted under 35 U.S.C. 154(b) by 443 days.

(21) Appl. No.: 13/855,964

(22) Filed: Apr. 3, 2013

(65) Prior Publication Data

US 2014/0303980 A1  Oct. 9, 2014

(51) Int. Cl.
A61B 5/00  (2006.01)

(52) U.S. Cl.
CPC ............ *A61B 5/4803* (2013.01); *A61B 5/6898* (2013.01); *A61B 5/7235* (2013.01); *A61B 5/7282* (2013.01)

(58) Field of Classification Search
CPC ... A61B 5/4803; A61B 5/7235; A61B 5/7282
See application file for complete search history.

(56) References Cited

U.S. PATENT DOCUMENTS

| | | | | |
|---|---|---|---|---|
| 4,593,019 A | * | 6/1986 | Bristol et al. | 514/46 |
| 4,694,007 A | * | 9/1987 | Allegra et al. | 514/266.4 |
| 5,442,146 A | * | 8/1995 | Bell et al. | 177/210 FP |
| 5,574,639 A | * | 11/1996 | Qian et al. | 708/300 |
| 5,696,875 A | * | 12/1997 | Pan et al. | 704/219 |
| 5,701,391 A | * | 12/1997 | Pan et al. | 704/212 |
| 5,809,453 A | * | 9/1998 | Hunt | 704/214 |
| 5,960,102 A | * | 9/1999 | Van Eeuwijk et al. | 382/128 |
| 6,434,520 B1 | * | 8/2002 | Kanevsky et al. | 704/243 |
| 7,398,213 B1 | | 7/2008 | Levannon et al. | |
| 7,529,670 B1 | * | 5/2009 | Michaelis | 704/253 |
| 7,814,029 B1 | * | 10/2010 | Siegel | 705/347 |
| 2003/0130843 A1 | * | 7/2003 | Ky | 704/235 |
| 2004/0054539 A1 | * | 3/2004 | Simpson | 704/270.1 |
| 2004/0107079 A1 | * | 6/2004 | MacAuslan | 703/2 |
| 2004/0107104 A1 | * | 6/2004 | Schaphorst | 704/270 |
| 2004/0167774 A1 | | 8/2004 | Shrivastav | |
| 2004/0210159 A1 | * | 10/2004 | Kibar | 600/558 |
| 2005/0049876 A1 | * | 3/2005 | Agranat | 704/270 |
| 2005/0060155 A1 | * | 3/2005 | Chu et al. | 704/269 |
| 2006/0116878 A1 | * | 6/2006 | Nagamine | 704/239 |

(Continued)

OTHER PUBLICATIONS

Google Search: voice analysis throat cancer detect: Article by: Ibach, Susan "Could a phone app detect throat cancer?", Dated Sep. 11, 2012, (1 page).

*Primary Examiner* — Eric Yen
(74) *Attorney, Agent, or Firm* — Ulmer & Berne LLP

(57) ABSTRACT

A system and method for assisting in a determination of one or more maladies associated with a human voice anatomy utilizes voice information acquired over at least two temporally displaced acquisitions. Acquired voice samples, including plural vowel sounds, are digitized and passed through one or more bandpass filters to isolate one or more frequency ranges. Curve fitting of acquired data is completed in accordance with a plurality of parameter weights applied in either a time domain or frequency domain model of the voice. This process is repeated a second, later time, for the same human, and the same process is completed for the subsequently-acquired voice information. A difference between the curve information in the respective data sets is analyzed relative to the weights, and corresponding changes are correlated to maladies of various areas of the human voice anatomy.

14 Claims, 6 Drawing Sheets

(56) References Cited

U.S. PATENT DOCUMENTS

| | | | |
|---|---|---|---|
| 2006/0284069 A1* | 12/2006 | Le Blanc | 250/282 |
| 2007/0265533 A1* | 11/2007 | Tran | 600/481 |
| 2008/0101722 A1* | 5/2008 | Bryll et al. | 382/278 |
| 2010/0261456 A1* | 10/2010 | Stakutis et al. | 455/412.2 |
| 2012/0215454 A1* | 8/2012 | Yang et al. | 702/19 |
| 2012/0220899 A1 | 8/2012 | Oh et al. | |
| 2013/0166291 A1* | 6/2013 | Lech et al. | 704/232 |

\* cited by examiner

SYSTEM AND METHOD FOR AUDIO KYMOGRAPHIC DIAGNOSTICS

TECHNICAL FIELD

The subject application is directed generally to analysis of the human voice generation mechanism in accordance with changes between temporally displaced voice samples. The application is particularly applicable to diagnosis of human voice anatomy maladies, extending to the point of determining what portion of the voice generation mechanism is likely causing the problem or malady.

BACKGROUND

The human voice forms a central aspect of our society. It is a critical tool for social interaction, learning and entertainment. Loss or impairment of one's ability to speak requires significant challenges and adaptations.

A voice is defined as sounds from a human being. Such sounds include talking, laughing, screaming, humming, singing, and the like. Voice generation is accomplished by expelling air from the lungs though the vocal cords of the larynx, also referred to as the voice box. The human voice emanates from the glottis. The glottis is defined as the vocal cords and the space between the associated folds. The glottis is comprised of several portions, including the larynx and the vocal cords. Maladies that affect one's ability to speak include glottis stenosis, various cancers, vocal cord nodes, laryngeal nodules, as well as an array of other possible disorders.

Voice-related problems may be followed by symptoms such as: dysphagia, or trouble swallowing; odynophagia, or pain in swallowing; lumps in one's neck; dyspnea, or difficulty in breathing; or otalgia or ear pain. In many instances, once these symptoms arise, a disease may have progressed to the point where treatment is ineffective, unavailable or incomplete. Early detection and diagnosis provides significant advantages in connection with treatment and recovery.

Some aspects of voice-related problems may be discernible by a doctor examining a patient's throat. However, since much of the voice generation mechanism, including the glottis is not visible with such an examination, the doctor may rely on procedures such as laryngoscopy. In this procedure, a laryngoscope is inserted through a patient's mouth to view areas such as the vocal cords. However, such a procedure is not part of a typical medical test such as one might encounter during a regular physical and are typically completed only once symptoms, such as those noted above, have been experienced. Thus, many disease may not be diagnosed until they have achieved an advanced stage.

OVERVIEW OF EXAMPLE EMBODIMENTS

Figure 1:
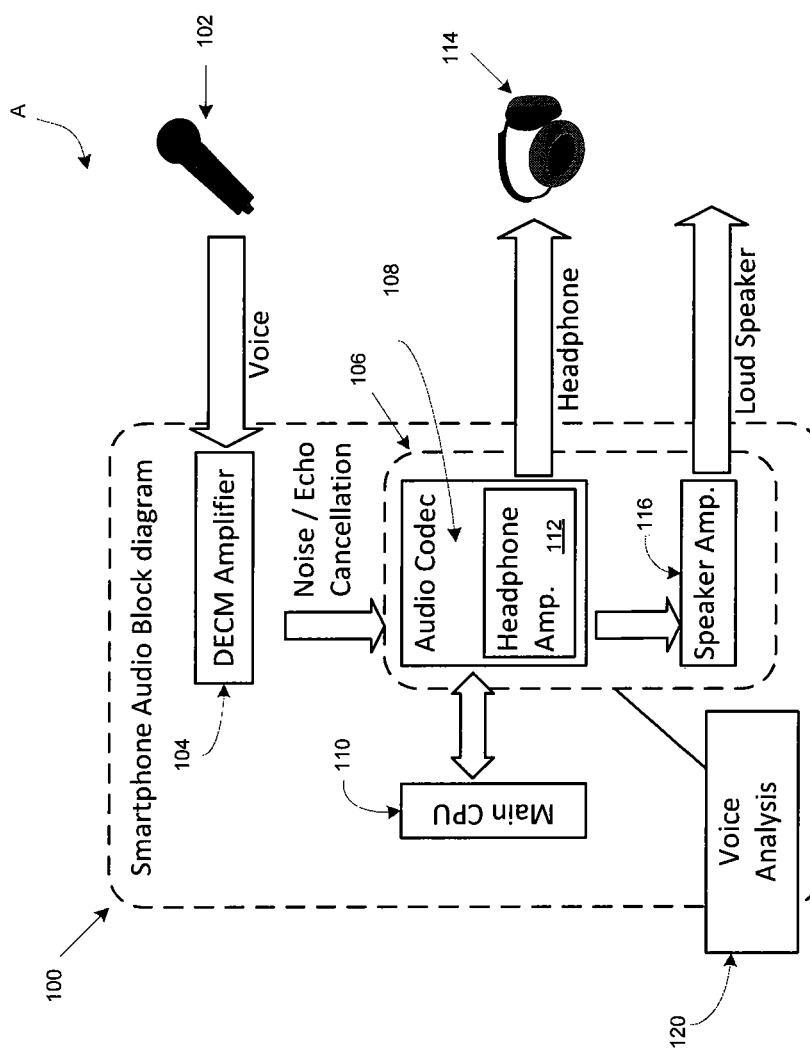
FIG. 1 is a block diagram of a suitable hardware environment in connection with an embodiment of the subject application.

An embodiment of the present application includes a diagnostic method and system that receives a first digitized human voice sample, associated with a target person, into an associated data storage. A first curve representation of the first digitized sample is determined in accordance with an associated wave domain. A curve fitting is applied to the first curve representation in accordance with a plurality of parameter weights and data representative of this fitting is stored. A second digitized human voice sample is then received from the target person and a second curve representation of the second digitized sample in accordance with an associated wave domain is determined therefrom. A curve fitting is applied to the second curve representation in accordance with the plurality of parameter weights and the results are stored. A difference value between the first curve fitting and the second curve fitting is calculated and the result is used to determine a vocal disorder.

In accordance with another embodiment, at least one pass band filter is applied to the first digitized human voice sample prior to determining the first curve representation such that it is determined for each of a first plurality of bands. Similarly, at least one pass band filter is applied to the second digitized human voice sample prior to determining the second curve representation such that the second curve representation is determined for each of a second plurality of bands.

In accordance with another embodiment, each parameter weight of the plurality is associated with a unique area of a human voice generation system such that a determined vocal disorder is associated with at least one unique area in accordance with a calculated difference value.

In accordance with another embodiment, the calculated difference value includes identification of at least one of a difference of amplitude or frequency relative to a corresponding band.

In accordance with another embodiment, a vocal disorder is determined by comparison of difference values with at least one preselected range value associated with at least one vocal disorder.

In accordance with another embodiment, each curve fitting is applied in accordance with a plurality of fractional weight reductions to each of the parameter weights so as to generate each corresponding curve fitting.

In accordance with another embodiment, the parameter weights are adjusted in accordance with parameter values.

DESCRIPTION OF EXAMPLE EMBODIMENTS

Sounds are defined as a propagation of vibrations, travelling as waves, through a medium. When that medium is air, sound waves travel by compression and rarefaction of air molecules.

Earlier voice communication systems, including radio and telephone communication systems, were entirely analog, capturing, amplifying and propagating wave forms, such that an output wave form from a speaker output would be ideally as close as possible to an incoming wave form from a microphone input. Earliest electronic voice communication was "near real time," that is to say, the listener received the voice information shortly after it was rendered, no storage being employed in the process other than propagation delay.

Audio capture has been available for many years. Earlier systems, such as phonographs, functioned to capture and record sound mechanically. Later, audio capturing used electronics and electromagnetics to capture sound information, and included electronic amplification, electronic transmission and magnetic tape storage. More recently, numeric representation of captured sound is accomplished by sampling one or more captured sound waves and sampling them over a domain, such as a time or frequency domain. Each sampling results in a magnitude value, suitably stored as a binary number. This is suitably accomplished by an analog-to-digital (A/D) converter as will be appreciated by one of ordinary skill in the art. Many A/D converters exist, having various properties relative to sampling rate, resolution and input signal sensitivity, and the like.

Today, most communication systems are digital in at least some, if not all, of the transmission process. Newer generation cellular telephone communications are digitized immediately upon voice capture, and remain digital until sound information is recreated at a receiving end by a digital-to-analog (D/A) converter. Even older, analog telephone sets, which may capture and transmit an analog signal, are typically converted to digitized sound for transmission. Modern voice mail systems typically store a digitized rendering, either on a phone device, on a dedicated storage such as an answering machine, or on a server associated with a communications provider. Accordingly, many cellphones or handsets can provide a digital representation of a human voice without any additional equipment.

In addition to the afore-noted advances in digital sound capture and storage, there has been a persistent, rapid growth in digital processing capabilities, both in the rapid increase of available processing power and in data storage capability. Additionally, as these capabilities improve, cost, power consumption and hardware size continues to shrink. As to cell phones, processing power is available both at the device, and in the "cloud" where digital communications are relayed, processed and stored.

An embodiment of the subject application leverages the forgoing to provide a system and method for determining, and another embodiment for pinpointing, maladies of the human voice generation areas by leveraging readily available platforms in a comfortable user environment.

Turning now to FIG. 1, illustrated is a suitable hardware environment in connection with an embodiment of the subject application. In the illustration, a digital sound processing system A is an audio capture system 100, suitably comprised of a smartphone. Voice input 102 is communicated to a receiver/amplifier 104, and suitably subject to a noise/echo cancellation system 106. The noise/echo cancellation system 106 suitably includes an audio codec (code/decode) system 108, suitably inclusive of software system operable in conjunction with at least one processor, such as that noted as CPU 110. Also suitably included with the noise/echo cancellation system 106 is an output amplifier, such as headphone amplifier 112, suitable to drive an earpiece or headphone outlet 114. Also illustrated is a speaker amplifier 116, which may be a separate amplifier, or share components with the headphone amplifier 112 as will be appreciated by one of ordinary skill in the art. The speaker amplifier 116 is suitable to drive an associated loudspeaker, or any other suitable electric/sound transducer. Also illustrated in FIG. 1 is a voice analysis system 120 which suitably interacts with the noise/echo cancellation system 106 or the main CPU 110 as will be detailed further below.

Figure 2:
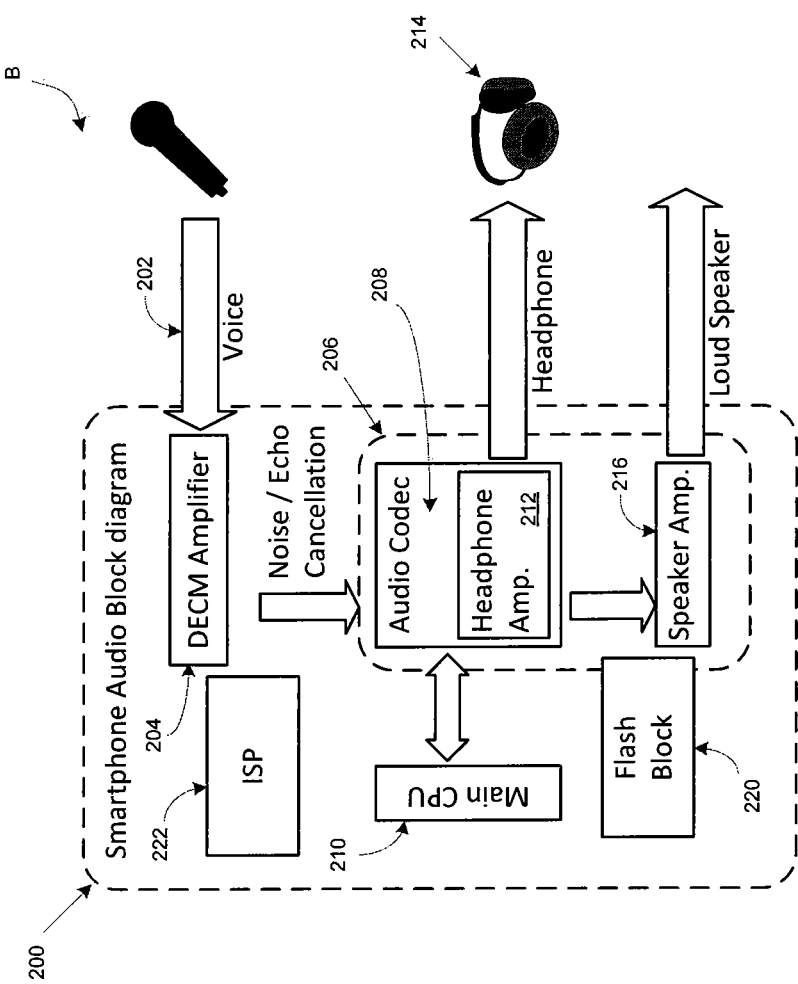
FIG. 2 is a block diagram of a suitable hardware environment in connection with another embodiment of the subject application.

Turning now to FIG. 2, another suitable hardware embodiment is illustrated. As with the embodiment of FIG. 1, a digital sound processing system B is an audio capture system 200, suitably comprised of a smartphone. Voice input 202 is communicated to a receiver/amplifier 204, and suitably subject to a noise/echo cancellation system 206. The noise/echo cancellation system suitably includes an audio codec (code/decode) system 208, suitably inclusive of software system operable in conjunction with at least one processor, such as that noted as CPU 210. Also suitably included with the noise/echo cancellation system 206 is output amplifier, such as headphone amplifier 212, suitable to drive an earpiece or headphone outlet 214. Also illustrated is a speaker amplifier 216, which may be a separate amplifier, or share components with the headphone amplifier 212 as will be appreciated by one of ordinary skill in the art. The speaker amplifier 216 is suitable to drive an associated loudspeaker or any other suitable electric/sound transducer. In the embodiment of FIG. 2, a voice analysis platform, flash block 220 and ISP/block 222, cooperate to derive the results in a fashion as will be detailed further below. Block 220 comprises an array of non-volatile memory elements which is used to store calibration coefficients after each curve fitting iteration. The flash block 220 is linked to CPU block 210 with a peripheral bus that also links to the ISP block 222. ISP block 222 is a signal processing block that contains the machine learning algorithms that are applied to the processed voice data. This block also is connected to block 204, block 206, and block 210.

Figure 3:
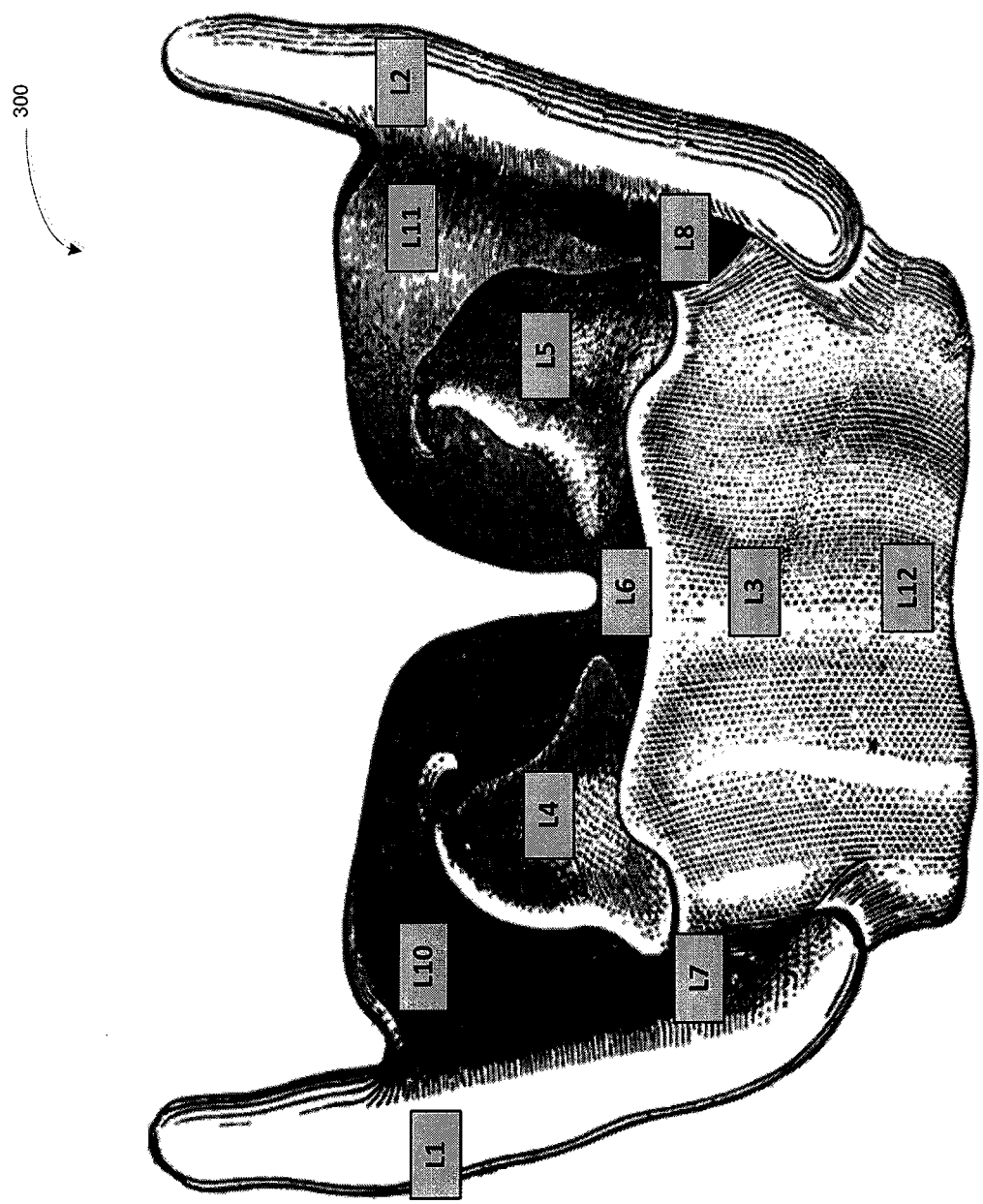
FIG. 3 is a rendering of a human glottis with areas of an embodiment suitable for mathematical modeling in connection with the subject application.

Turning now to FIG. 3, illustrated is a pictorial view of the human glottis wherein segmentation has been noted to facilitate mathematical modeling as will be detailed below, and which segmentation facilitates isolation of potential maladies to one or more areas of the entire voice-generating mechanism. It will be appreciated by one of ordinary skill in the art that the illustrated glottal portion is a representative portion of the human voice area only. Any portion of that area is suitable for analysis in conjunction with the teachings herein.

In FIG. 3, representative areas of a section of the vocal generation area 300 are marked as an example of mathematical modeling areas in conjunction with the teachings of the subject application. In the illustration, representative, isolated portions are suitably referred to as:

L1—L superior horn of thyroid cartilage
L2—R superior horn of thyroid cartilage
L3—Superior aspect of cricoid cartilage
L4—L arytenoid cartilage
L5—R arytenoid cartilage
L6—Superior thyroid notch
L7—L inferior horn of thyroid cartilage
L8—R inferior horn of thyroid cartilage
L10—L superior thyroid tubercle
L11—R superior thyroid tubercle
L12—Inferior aspect of cricoid cartilage It will be appreciated that the depictions and area selections of the illustration of FIG. 3 are representative of many possible sub areas, as well as representative of a selected portion of the human voice generation system. It will be appreciated by one of ordinary skill in the art that isolation of selected portions of the entire voice generation system is contemplated and disclosed in connection with the teachings herein.

Figure 4:
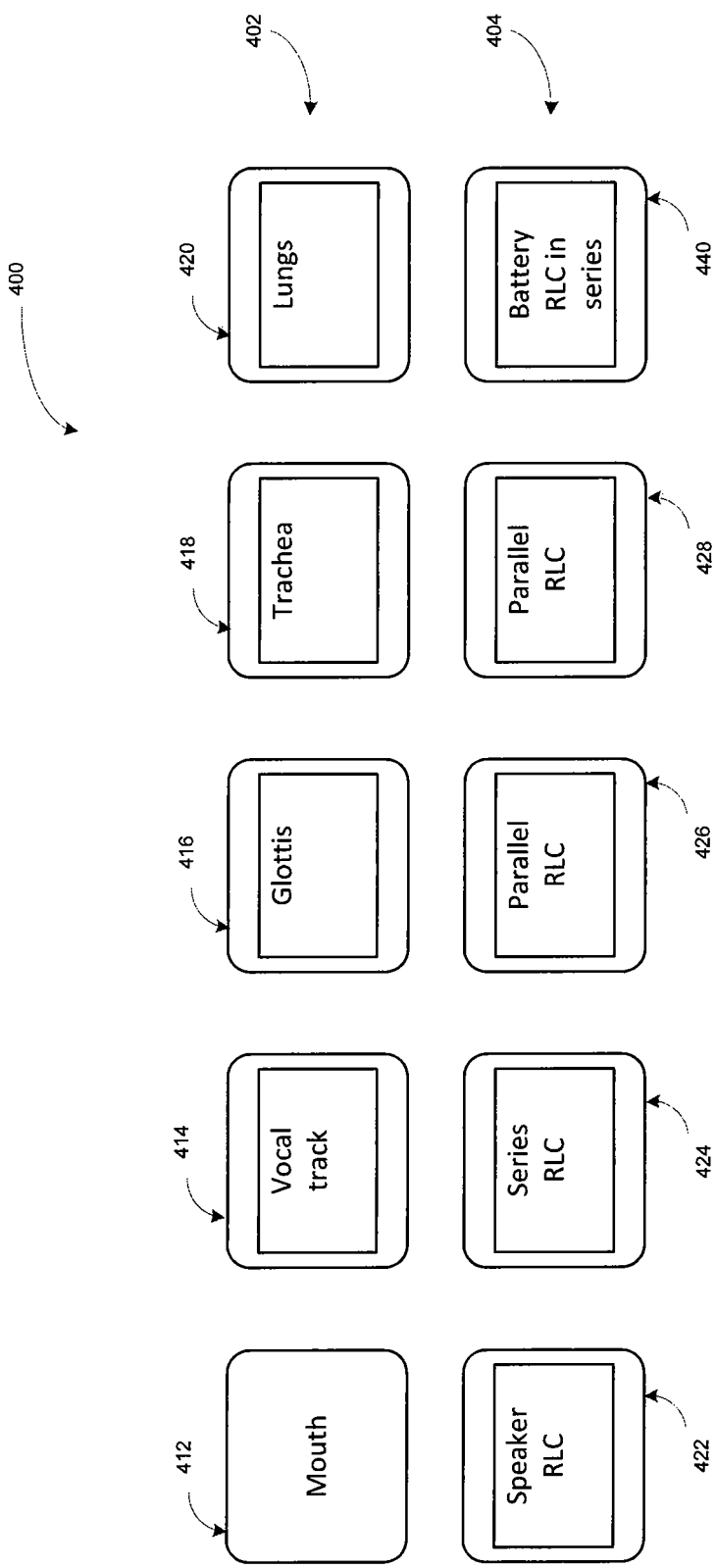
FIG. 4 shows an embodiment of potential mathematical modeling of the human voice box in connection with the subject application.

Turning to FIG. 4, depicted is an abstraction of an embodiment of mathematical modeling schema 400 with representative areas of the human vocal areas 402 and corresponding, electronic circuit related mathematical models 404. Included areas are mouth 412, vocal track 414, glottis 416, trachea 418 and lungs 420. It will be appreciated that the embodiment of FIG. 4 is illustrative of one possible grouping of voice-related areas. Any or all voice-generating areas are suitably utilized and modeled in accordance with an application-specific need or desire as will be appreciated by one of ordinary skill in the art.

As illustrated in the embodiment of FIG. 4, each representative vocal area 412, 414, 416, 418 and 420 is associated, in order, with mathematical models 422, 424, 426, 428 and 440. Each mathematical model is associated with an electronic resistor-inductor-capacitor (RLC) circuit in the illustrated embodiment, which circuit is suitably supplemented by additional electrically-related components in certain instances, such as a power source or audio transducer such as a speaker, headset, earphones or microphone.

Mouth area 412 is suitably modeled with an RLC circuit 422 working in concert with an associated speaker or any other suitable audio transducer, such as an earphone, headset or the like. Vocal track area 414 is suitably modeled with a series RLC circuit 424. Glottis area 416 is suitably modeled with parallel RLC circuit 426. Trachea area 418 is suitably modeled with parallel RLC circuit 428. Lung area 420 is suitably modeled with RLC circuit 440 working in concert with a suitable forcing function or power source, such as a battery, current source, or voltage source. Values associated with electronic or electromechanical model components are set corresponding to received sound properties as will further detailed below.

Figure 5:
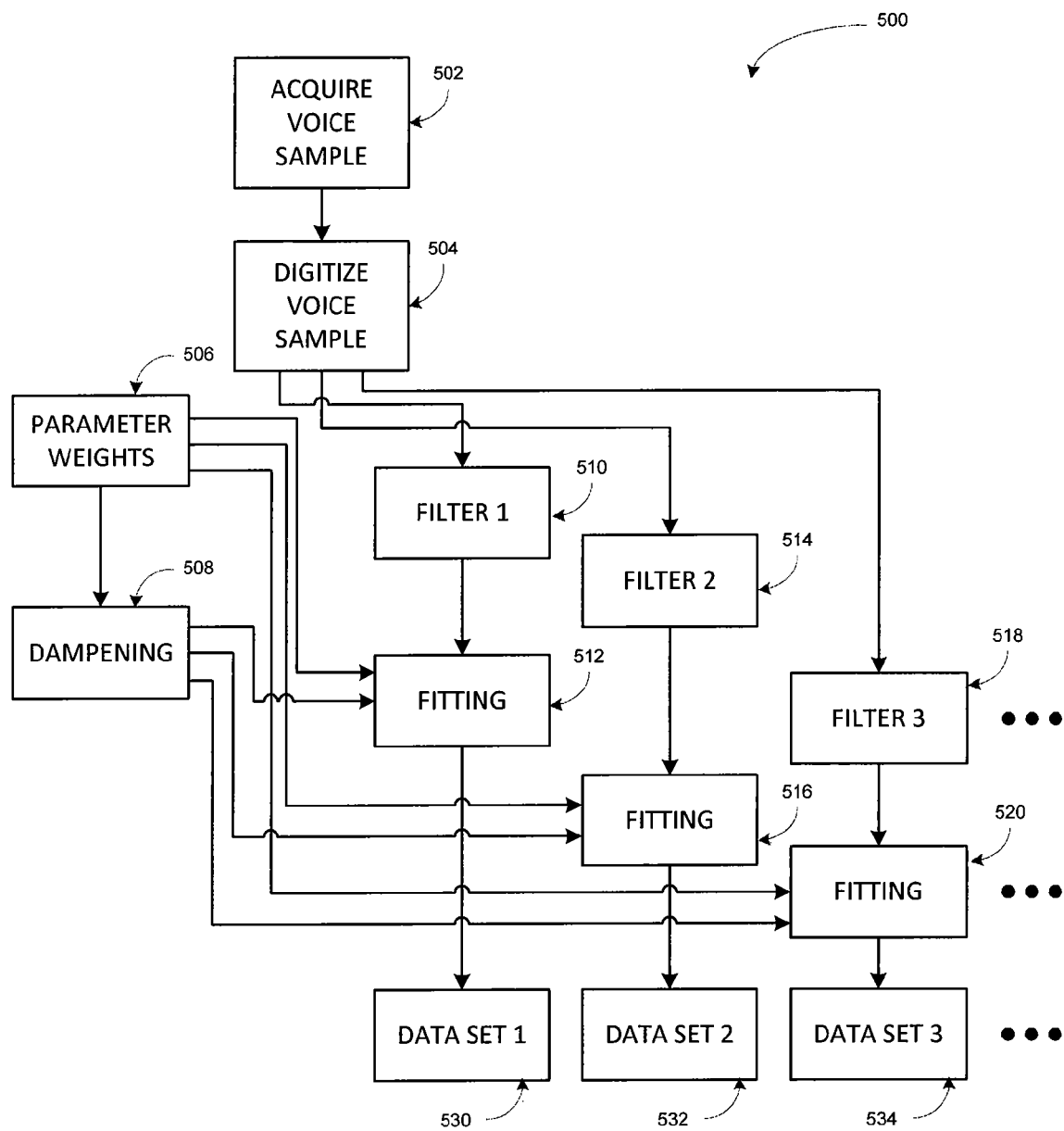
FIG. 5 is a flow chart for voice acquisition, filtering and curve fitting in connection with an embodiment of the subject application.

Turning now to FIG. 5, illustrated is a flow diagram for voice analysis in connection with an embodiment of a voice analysis system 500 of the subject application. The system commences by acquiring a voice sample at block 502, referred to herein as a voice sample under test (VoTinit). As will be detailed below and as noted above, the subject application teaches an embodiment wherein multiple voice samples are acquired over time. The illustrated embodiment herein will be appreciated to facilitate mathematical modeling and analysis for each such acquired voice sample.

As noted above, any suitable electromechanical transducer is operable in connection with receipt of a signal representative of an associated voice. This signal is suitably digitized at block 504 by any suitable ND converter as will be appreciated by one of ordinary skill in the art. As noted above, this, as well as other components herein, are suitably preexisting in a device such as a cellphone, computer, handset, or the like. Digitized voice data is suitably streamed, or packet or block based, such as in communication protocols including, but not limited to TCP/IP. The voice data is also suitably referenced in a time domain or a frequency domain. As will be appreciated by one of ordinary skill in the art, conversion between domains is also contemplated in accordance with an application of a suitable transform function, such as a Fourier transform suitably accomplished with a fast Fourier transform.

A suitable mathematical model for voice input is accomplished by construction of a voice-sample-under-test signature (VOoTsignature) by assigning coefficients associated with voice sample characteristics to a modeling equation. A digitized voice sample is suitably used to generate one or more associated data sets via application of selective filtering and curve fitting, suitably in connection with application of associated parameter weights 506 and dampening 508. As illustrated in FIG. 5, a digitized voice sample is suitably communicated to filter 1 510 suitably receiving parameter weight data, resulting in a curve fitting 512 in connection with dampening data 508. Two or more data sets are also suitably generated in connection with subsequently received voice data inputs via filter 2 514 operating in connection with fitting 516, filter 3 518 operating in connection with fitting 520, and the like. In the illustrated embodiment, the resultant data sets, data set 1 530, data set 2 532, data set 3 534, etc., are thus generated.

Dampening is suitably accomplished by a structured reduction of weights wherein the resulting calculations are used to generate a composite signal. In an example embodiment, weights are iteratively reduced by ¼, ½ and ¾, and these weights are used in connection with calculating damped curves in connection with filter operations.

Suitable filtering in accordance with the forgoing is completed with bandpass filters. In a representative embodiment, a first filtering is accomplished with a low pass filter, suitably 0.5 to 1 kHz. A second filtering is accomplished with a pass band filter generally in the range of 1 to 1.5 kHz. A third filtering is suitably accomplished in the pass band of 3.5 to 4 kHz. It will be appreciated that such filter ranges are representative only of an example embodiment. Numbers of filter operations and particular ranges associated with each are suitably altered and optimized in accordance with a particular application. Suitable sampling is subject for analysis up to the general range of human hearing at 20 kHz, even extending to ultrasonic frequencies in selected embodiments. Such damped curves suitably form baselines for comparative analysis relative to subsequently captured waveforms.

By way of example, a suitable voice waveform representation is:

$$VoTsignture = \alpha L1 + \beta L2 + \ldots + \omega L12$$

wherein $\alpha, \beta, \ldots$ are coefficients and wherein $L1, L2, \ldots$ suitably represent properties including amplitude, wavelength, period length, frequency or any other suitable waveform characteristic. Coefficients also suitably represent code strength for any suitable coding scheme, including but not limited to pulse-amplitude modulation (PAM), pulse-width modulation (PWM), pulse code modulation (PCM), frequency-shift keying (FSK), or any other suitable coding scheme as will be appreciated by one of ordinary skill in the art.

Figure 6:
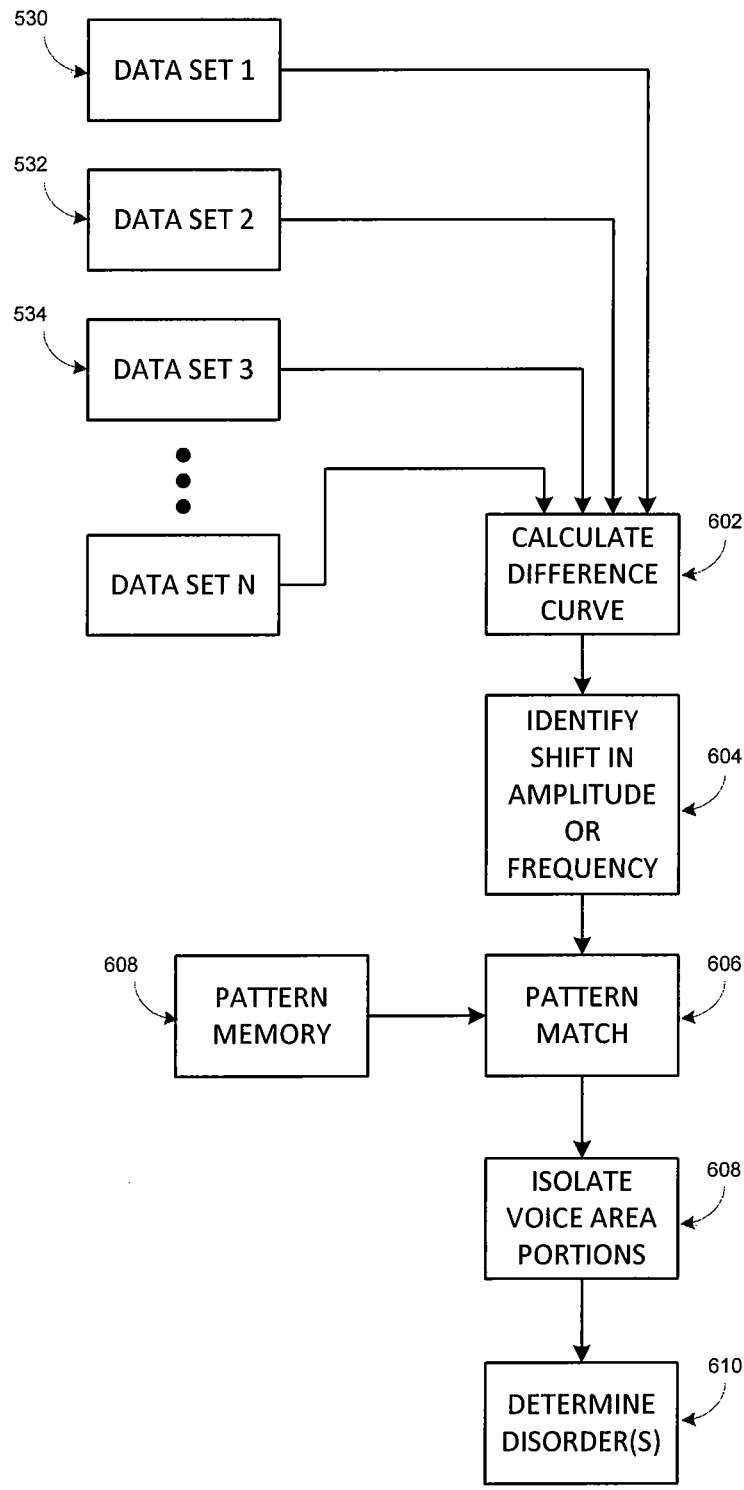
FIG. 6 is a flow chart for identification of voice changes or aberrations in connection with an embodiment of the subject application.

Turning now to FIG. 6, it will be noted that data set 1 530, data set 2 532, data set 3 534, . . . data set N are received in connection with two or more voice inputs, and subject to weighting and dampening as detailed above. Difference curves are calculated at 602, and variations are determined, such as shift in amplitude, frequency or other suitable wave characteristic, at 604. The results are subject to a pattern match 606, which match is completed in connection with content of a pattern memory 608, suitably formed of empirical data indicators representative of waveform variations that are associated with voice area maladies. Once isolated at 610, a suitable indicator is generated to evidence any isolated or identified malady, along with an area in which the malady is associated.

The invention claimed is:
1. A diagnostic method comprising:
receiving a first digitized human voice sample, associated with a target person, into an associated data storage;
determining a first curve representation of the first digitized sample in accordance with an associated wave domain;
applying a curve fitting to the first curve representation in accordance with a plurality of parameter weights;
storing data representative of the first curve fitting;
receiving a second digitized human voice sample from the target person;
determining a second curve representation of the second digitized sample in accordance with an associated wave domain;

applying a curve fitting to the second curve representation in accordance with the plurality of parameter weights;
storing data representative of a second curve fitting;
calculating a difference value between the first curve fitting and the second curve fitting; and
determining a vocal disorder in accordance with a calculated difference value.

2. The method of claim 1 further comprising:
applying at least one pass band filter to the first digitized human voice sample prior to the step of determining the first curve representation such that the first curve representation is determined for each of a first plurality of bands thereof; and
applying the at least one pass band filter to the second digitized human voice sample prior to the step of determining the second curve representation such that the second curve representation is determined for each of a second plurality of bands thereof.

3. The method of claim 2 further wherein each parameter weight of the plurality is associated with a unique area of a human voice anatomy such that a determined vocal disorder is associated with at least one unique area in accordance with a calculated difference value associated therewith.

4. The method of claim 3 wherein each calculation of the difference value includes identification of at least one of a difference of amplitude or frequency relative to a corresponding band.

5. The method of claim 4 wherein determining a vocal disorder includes comparing difference values with at least one preselected range value associated with at least one vocal disorder.

6. The method of claim 5 wherein each curve fitting is applied in accordance with a plurality of fractional weight reductions to each of the parameter weights so as to generate each corresponding curve fitting as composite thereof.

7. The method of claim 6 further comprising adjusting the parameter weights in accordance with parameter values.

8. A diagnostic system comprising:
an input operable to receive a first digitized human voice sample, associated with a target person, into an associated data storage;
a processor operable to determine a first curve representation of the first digitized sample in accordance with an associated wave domain;
the processor further operable to apply a curve fitting to the first curve representation in accordance with a plurality of parameter weights;
a memory operable to store data representative of the first curve fitting;
the input being further operable to receive a second digitized human voice sample from the target person;
the processor further operable to determine a second curve representation of the second digitized sample in accordance with an associated wave domain;
the processor further operable to apply a curve fitting to the second curve representation in accordance with the plurality of parameter weights;
the memory further operable to store data representative of a second curve fitting;
the processor further operable to calculate a difference value between the first curve fitting and the second curve fitting; and
an output operable to output a signal representative of a vocal disorder in accordance with a calculated difference value.

9. The system of claim 8 further comprising:
at least one pass band filter operable to be applied to the first digitized human voice sample prior to a determination of the first curve representation such that the first curve representation is determined for each of a first plurality of bands thereof; and
the at least one pass band filter being further operable to be applied to the second digitized human voice sample prior to a determination of the second curve representation such that the second curve representation is determined for each of a second plurality of bands thereof.

10. The system of claim 9 wherein each parameter weight of the plurality is associated with a unique area of a human voice anatomy such that a determined vocal disorder is associated with at least one unique area in accordance with a calculated difference value associated therewith.

11. The system of claim 10 wherein the processor is further operable to calculate the difference value in accordance with at least one of a difference of amplitude or frequency relative to corresponding band.

12. The system of claim 11 wherein the processor is further operable to compare difference values with at least one preselected range value associated with at least one vocal disorder.

13. The system of claim 12 wherein each curve fitting is applied in accordance with a plurality of fractional weight reductions to each of the parameter weights so as to generate each corresponding curve fitting as composite thereof.

14. The system of claim 13 wherein the processor is further operable to adjust the parameter weights in accordance with parameter values.

* * * * *